United States Patent
Fujioka et al.

[19]

[11] Patent Number: 5,851,547
[45] Date of Patent: Dec. 22, 1998

[54] CONTROLLED RELEASE DRUG FORMULATION OF OPEN END CYLINDRICAL ROD FORM

[75] Inventors: Keiji Fujioka, Hyogo Prefecture; Takeshi Hirasawa, Osaka Prefecture; Masako Kajihara, Hyogo Prefecture; Akihiko Sano, Osaka Prefecture; Shuichi Sugawara, Kanagawa Prefecture; Yosuke Urabe, Kanagawa Prefecture, all of Japan

[73] Assignees: Dow Corning Asia, Ltd., Tokyo; Sumitomo Pharmaceuticals Co., Ltd., Osaka, both of Japan

[21] Appl. No.: 762,847

[22] Filed: Dec. 10, 1996

Related U.S. Application Data

[63] Continuation of Ser. No. 362,623, Dec. 22, 1994, abandoned.

[30] Foreign Application Priority Data

Dec. 27, 1993 [JP] Japan .................................. 5-331467

[51] Int. Cl.⁶ ............................................. A61K 9/24
[52] U.S. Cl. ........................ 424/426; 424/423; 424/424
[58] Field of Search ............................................. 424/426

[56] References Cited

U.S. PATENT DOCUMENTS

| | | | |
|---|---|---|---|
| 3,710,795 | 1/1973 | Higuchi et al. | 128/260 |
| 3,926,118 | 12/1975 | Preuss . | |
| 4,191,741 | 3/1980 | Hudson et al. . | |
| 4,351,337 | 9/1982 | Sidman . | |
| 4,891,223 | 1/1990 | Ambegaonkar et al. . | |
| 4,985,253 | 1/1991 | Fujioka et al. | 424/488 |
| 5,395,618 | 3/1995 | Darougar et al. . | |

FOREIGN PATENT DOCUMENTS

| | | |
|---|---|---|
| 0226884 | 7/1987 | European Pat. Off. . |
| 0250374 | 12/1987 | European Pat. Off. . |
| 042519 | 5/1991 | European Pat. Off. . |
| 5513381 | 3/1980 | Japan . |
| 2142738 | 5/1990 | Japan . |
| 0346120 | of 1992 | Japan . |
| 4364120 | 12/1992 | Japan . |
| 6-321803 | 11/1994 | Japan . |
| 8909066 | 10/1989 | WIPO . |

OTHER PUBLICATIONS

Robertson et al May 1983 vol. 27 No. 5 Contraception.
Hseih et al., *Pharmaceutical Technology*, pp. 39–49, Jun. 1985.
Rhine et al., *Journal. Pharm. Sci.*, vol. 69, No. 3, Mar. 1980.
Robertson et al., *Contraception*, vol. 27, No. 5, pp. 483–495, May 1983.
Carelli et al., *Int. Journ. Pharm.*, Vol. 50, pp. 181–188, 1989.
Rhine et al., *Journ. Pharm.*, vol. 69, No. 3, pp. 265–270, Mar. 1980.
Miyazaki et al., *Chem. Pharm. Bull.*, vol. 29, No. 9, pp. 2714–2717, 1981.

*Primary Examiner*—Peter F. Kulkosky
*Attorney, Agent, or Firm*—Birch, Stewart, Kolasch and Birch, L.L.P.

[57] ABSTRACT

A drug formulation for producing sustained therapeutic efficacy, which releases at least one water-soluble drug over a prolonged period of time at a substantially constant rate wherein said drug formulation comprises (a) a nondisintegrating inner layer comprised of a biocompatible material that contains at least one uniformly dispersed water-soluble drug; and (b) an outer layer comprised of a biocompatible material that surrounds the circumference of the said inner layer, is impermeable to water, and is capable of controlling the swelling of the inner layer; wherein the ratio of the axial length of the drug formulation to the cross-sectional diameter of the inner layer is one or more and wherein one or both ends of the inner layer are open so as to come into direct contact with the external environment.

23 Claims, 3 Drawing Sheets

CONTROLLED RELEASE DRUG FORMULATION OF OPEN END CYLINDRICAL ROD FORM

This application is a continuation of application Ser. No. 08/362,623, filed Dec. 22, 1994, which application is now abandoned.

BACKGROUND OF THE INVENTION

As a result of recent advances in biotechnology, drug therapy using proteinaceous drugs has become important. Most proteinaceous drugs exhibit very short half-lives in the blood, e.g., a few minutes to a few hours, and as a result it becomes necessary to administer them at frequent intervals in order to achieve long-term maintenance of the drug concentration in the blood within therapeutic ranges. One problem generally associated with the drug formulations known up to now is that the drug concentration in the blood immediately after administration can reach levels which may produce negative effects, and frequent administration thus tends to increase the frequency of occurrence of side effects. In addition, the use of injectable drug formulations of this type places a very heavy burden on the patient because it requires frequent hospital treatment or outpatient visits and causes pain at the time of administration.

Given the foregoing circumstances, it is desirable to develop a controlled release drug formulation that is capable of maintaining the therapeutic efficacy of water-soluble drugs, such as proteins, over prolonged periods after a single administration.

The use of polymeric materials as drug carriers is the most common technology for sustained drug release systems, where the main goal is the maintenance of sustained therapeutic efficacy in the body. In systems in which the drug is dispersed in a hydrophobic polymer carrier, the release mechanism for lipophilic drugs, which are capable of spontaneous diffusion through the carrier, is completely different from that for a water-soluble drug dispersed in the carrier since water-soluble drugs cannot spontaneously diffuse through the carrier. Achieving the controlled release of lipophilic drugs is relatively straightforward since these drugs can diffuse through polymer carriers (*Contraception*, volume 27, number 5, pages 483–495 (May, 1983), *Chem. Pharm. Bull.*, volume 29, number 9, pages 2714–2717 (1981)).

A channeling phenomenon participates in the release mechanism for water-soluble drugs from hydrophobic polymer carriers. Here, the drug present in the vicinity of the surface of the formulation first dissolves in the ambient water (body fluids and so forth). This step is followed by dissolution of the drug present around the resulting cavities, and the repetition of this process leads to the formation of continuous channels. In this case, the drug present in the interior of the formulation is released by diffusion through the resulting channels.

In one example of a technology whose goal is the controlled release of water-soluble drugs, V. Carelli et al. (*Int. J. Pharm.*, volume 50, pages 181–188 (1989)) reported that when sodium chloride was added to a silicone-matrix drug formulation containing a dispersed water-soluble drug for the purpose of inducing cracking by swelling, the water-soluble drug exhibited zero-order release as water penetrated into the drug formulation. However, because formulations of this type contain sodium chloride in large proportions, large volume changes will be produced by swelling in an aqueous medium. The use of such formulations in the body could be expected, for example, to induce stress in the surrounding tissues, thus making such devices unsuitable from a practical standpoint. In addition, the release rates were greatly accelerated, and these formulations were thus incapable of achieving sustained release over periods on the order of months. U.S. Pat. No. 4,985,253 discloses the control of drug release from silicone elastomers through the addition of albumin.

Unfortunately, the typical release behavior of matrix-type drug formulations consists of an initially high release rate due to the large effective release surface followed by a gradually declining first-order regime accompanying the decline in the effective release surface. This type of release behavior poses a particular problem in the case of formulations intended for implantation. Thus, while implants should be as small as possible in order to avoid foreign-body sensations and facilitate administration, reducing the diameter of a columnar drug formulation serves to increase the surface area relative to the volume. This results in an increase in the effective release area, which leads to further increases in the initial release rate. Such release behavior may be advantageous in some cases, depending on the disease and the drug; however, behavior of this type may cause problems in that the sudden initial increase in drug concentration may be associated with side effects and the time-wise variation in drug release may make management difficult. Accordingly, the development is desired of a zero-order-releasing drug formulation that achieves a more precise control of drug release and releases the drug for a prolonged period at a nearly constant rate.

While the following discussion contains examples of attempts to achieve controlled release with dosage forms other than the matrix type, none of these has been successful in achieving a practical zero-order release.

Dean S. T. Hsieh et al. (*J. Pharm. Sci.*, volume 69, number 3, pages 265–270 (1980)) reported the fabrication of an insulin-containing drug formulation by dispersing insulin in ethylene-vinyl acetate copolymer (EVA) and also reported the drug release behavior from this formulation after the entire surface had been coated with insulin-free EVA. However, as previously indicated, proteins such as insulin cannot diffuse through EVA, so insulin release would theoretically be impossible if the entire surface were coated with EVA. Therefore, the pertinent results, as noted by the authors themselves, derive from the fact that the device was not completely coated, and the effects of this drug formulation fabricated according to Dean S. T. Hsieh et al. are therefore uncertain or unclear.

A method is taught in Japanese Patent Laid-Open Number Hei 4-364120 [364,120/1992] for producing a drug formulation using collagen or gelatin as carrier. This drug formulation comprises a central part that contains the drug in the carrier and an outer wall part of collagen or gelatin, with the outer wall possibly containing a relatively low concentration of the drug.

European Patent Number 250374 teaches a sustained release system for the continuous release of a drug. This sustained release system comprises a water-swellable polymer that applies swelling pressure, a barrier capable of controlling the swelling, and the active ingredient. However, because the outer layers of these drug formulations are water permeable, they cannot achieve zero-order release over prolonged periods of time on the order of months.

European Patent Number 427519 teaches a drug delivery device consisting of a water-swellable polymer, a swelling regulator which controls the release, and the active ingredient. The essence of this invention is that swelling is controlled by the swelling regulator, and this in turn controls the rate of release of the active ingredient. An outer layer may be employed on an optional basis. However, the outer layers used consist of microporous or semipermeable membranes and are water permeable.

Japanese Patent Laid-Open Number Hei 2-142738 [142, 738/1990] teaches a drug formulation in which poly-alpha-amino acid is the drug carrier in the shape of an oriented-acicular form and a coating film of poly-alpha-amino acid is formed on the outer surface thereof. This invention does not refer to the water permeability of the coating film; however, when the entire outer surface is coated with polyleucine, which is a hydrophobic poly-alpha-amino acid, drug release occurs into physiological saline solution, and thus it is believed that water-permeable passages and/or drug-permeable passages are present. This invention also makes no report of the effects corresponding to the use of a water-impermeable and drug-impermeable outer layer.

Dean S. T. Hsieh et al. (*Pharmaceutical Technology*, June 1985, page 39) reported on the release of macromolecules from silicone elastomers, using devices obtained by fabricating matrix-type formulations in which a macromolecular substance was dispersed in silicone elastomer and covering the sides and one end of the formulation with silicone. These devices had button-shaped morphologies in which the diameter of the inner layer was approximately 8 mm (diameter including the outer layer =11 mm) and the axial length of the formulation was 5 mm. In the case of button-shaped devices having an axial length shorter than the diameter of the device's inner layer, it is impossible to satisfactorily control water infiltration. As a result, infiltration of water through the entire inner layer of the device occurs relatively rapidly, which makes it impossible to achieve the desired long-term zero-order release (see test examples below). This study does not disclose other shaped devices.

Thus, as discussed hereinbefore, although there have been numerous drug formulations that have attempted to achieve the controlled release of water-soluble drugs, up to now there has been no practical realization of a drug formulation or device that is capable of achieving zero-order release over prolonged periods of time.

It has now been discovered that controlling water infiltration (by, for example, body fluid or buffer) into the drug formulation is a key factor in being able to achieve long-term zero-order release of water-soluble drugs. Reducing the area of contact with water of course will come to mind as a means for controlling water infiltration. However, while such a tactic can by itself reduce the quantity of drug release, it cannot achieve long-term zero-order release.

It is an object of the instant invention to provide a drug-delivery formulation which releases a water-soluble drug intracorporeally over prolonged periods of time at a nearly constant rate (zero-order release) with the goal of producing sustained therapeutic efficacy.

SUMMARY OF THE INVENTION

The present invention relates to a controlled release drug formulation useful in medical treatment and livestock production. More specifically, the invention relates to a drug-delivery formulation which releases a water-soluble drug intracorporeally over prolonged periods of time at a nearly constant rate (zero-order release) with the goal of producing sustained therapeutic efficacy.

The object of the instant invention can be achieved through the use of a rod-like drug formulation comprising (a) a nondisintegrating inner layer comprised of biocompatible material that contains a uniformly dispersed water-soluble drug; and (b) an outer layer comprised of biocompatible material wherein the outer layer surrounds the circumference of the inner layer and said outer layer is impermeable to water and is capable of controlling the swelling of the inner layer;

wherein the ratio of the axial length of the drug formulation to the cross-sectional diameter of the inner layer is one or more and one or both ends of the inner layer are open so as to come into direct contact with the external environment.

Unlike the previous matrix-type drug formulations, in which water can infiltrate without any restriction into the interior of the drug formulation across the entire surface immediately upon contact with an aqueous medium, the rate of water infiltration is subjected to an optimal regulation in the drug formulation of the present invention. This functions to circumvent the problems described above, even for devices with small diameters, and makes it possible to achieve long-term zero-order release. Thus, the present invention facilitates development of practical drug formulations that combine two features: (i) simple, nonsurgical administration using an injector-type instrument, and (ii) the ability to maintain long-term efficacy.

THE INVENTION

Figure 1:
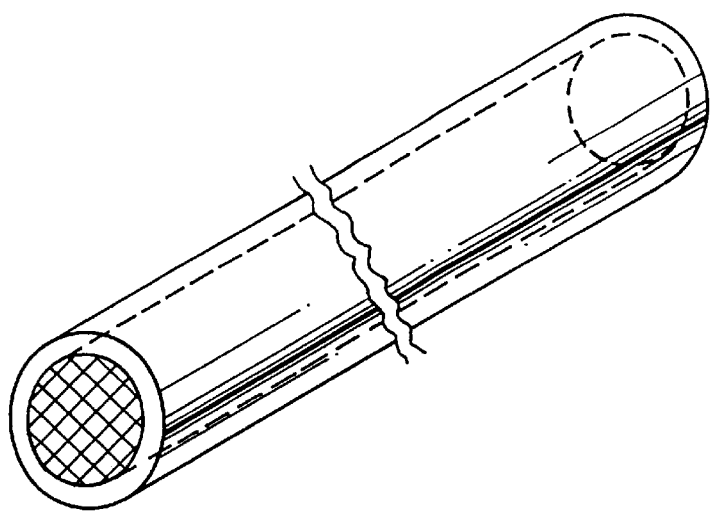
FIG. 1 contains an oblique view of one embodiment of the drug formulation of the present invention.

The instant invention relates to an implantable rod-like drug formulation comprising (a) a nondisintegrating inner layer comprised of a biocompatible material that contains a uniformly dispersed water-soluble drug; and (b) an outer layer comprised of a biocompatible material wherein said outer layer surrounds the circumference of the inner layer and said outer layer is impermeable to water and is capable of controlling the swelling of the inner layer;

wherein the ratio of the axial length of the drug formulation to the cross-sectional diameter of the inner layer is one or more and one or both ends of the inner layer are open so as to come into direct contact with the intracorporeal environment.

"Cross-sectional diameter" as used herein means, in the case of a circular cylinder, the diameter of the cross section taken at right angle to the axis ("right section" hereafter). In the case of a prism, the "cross-sectional diameter" means the length of the largest diagonal in the right section. In the case of an elliptical cylinder the "cross-sectional diameter" means the length of the major axis in the right section. "Axial length" as used herein refers to the distance between the two ends in axial direction of drug formulation. In addition, the expression "zero-order release" as used herein denotes an almost constant rate of release.

The release rate of water-soluble drug is controlled in the instant invention through control of water infiltration. Accordingly, the drug release rate may be controlled by any means capable of controlling water infiltration; for example, water infiltration can be controlled by suitable selection of the outer layer material or the thickness of the outer layer.

The outer layer material used in accordance with the present invention is not critical as long as it is biocompatible, is impermeable to water, and can control the swelling of the inner layer. Hydrophobic polymers are typically used for this purpose.

"Control of the swelling of the inner layer" refers to the maintenance of an appropriate pressure or constraint on the inner layer, and together with "impermeability to water" is a crucial factor in controlling water infiltration into the inner layer. Since the inner layer swelling rate varies widely as a function of the material properties of the carrier itself, the properties of the dispersed drug, any additive present in the interior, the mixing ratio and so on, material exercising the appropriate pressure must therefore be selected for the outer layer as a function of the aforementioned properties. The optimal pressure will vary according to the desired rate of release. Each of the outer layer materials indicated below can exhibit the desired pressure even without alteration of their native material properties. However, the drug release rate can also be fine-tuned by the addition of water-insoluble low-molecular-weight substances or by adjusting the thickness of the outer layer. For example, when silicone is chosen as the outer layer material, silica can be added in order to reduce the elasticity and increase the pressure applied to the swelling inner layer.

The outer layer material may be either a nonbiodegradable or biodegradable polymer, provided that any biodegradable polymer used does not permeate water during the period of drug release and retains its ability to control inner layer swelling during this same period. Biodegradable polymers with these properties can be easily obtained since the decomposition rate of biodegradable polymers can be varied by chemical modification and/or by varying the component ratios and/or by varying the molecular weight.

Biodegradable polymers that can be employed by the present invention may be exemplified by, but not limited to, polyesters such as poly(lactic acid-glycolic acid)copolymers (PLGA), etc. and by hydrophobic polyamino acids such as polyaranin, polyleucine etc., polyanhydride and the like. The hydrophobic polyamino acids mean polymers prepared from hydrophobic amino acid. The nonbiodegradable polymers may be exemplified by, but not limited to, silicones, polytetrafluoroethylenes, polyethylenes, polypropylenes, polyurethanes, polyacrylates, polymethacrylates such as polymethylmethacrylates, etc., ethylene-vinyl acetate copolymers, and others. More preferably, a silicone, for example, Silastic® Medical Grade ETR Elastomer Q7-4750 or Dow Corning® MDX 4-4210 Medical Grade Elastomer, is employed for the corresponding ease of molding. Even if these materials are used, there are instances where the outer layer may have a water-permeable and/or drug permeable hole due to insufficient thickness thereof, a crack caused by shrinkage during the drying process or the presence of bubbles. In this case it is required to apply a treatment such as repeating the process for formation of the outer layer until water and drug do not permeate through the outer layer.

The inner layer material may be an intrinsically water-swelling material, or it may consist of an intrinsically water-nonswelling material where the dispersed drug and/or a dispersed swelling agent absorbs water thereby swelling the inner layer as a whole. The inner layer material may be either biodegradable or nonbiodegradable, but in either case must be nondisintegrating. As used in the present specification, "nondisintegrating" means that the material does not immediately disappear upon contact with water, due for example to dissolution, degradation, etc., and is thereby able to retain its original shape for the desired period of time.

Biodegradable materials may be exemplified by, but not limited to, polyesters such as poly(lactic acid-glycolic)acid copolymers (PLGA) and by polyamino acids. Nonbiodegradable materials may be exemplified by, but not limited to, silicones, ethylene-vinyl acetate copolymers, polyvinyl alcohols and so on. Water-swelling materials may be exemplified by, but not limited to, polyvinyl alcohols and so forth. When a biodegradable polymer is employed, the biodegradable polymer must be one that releases the drug even without degradation and that will not undergo such a rapid degradative absorption that the swelling rate during the drug release period undergoes variation. Silicone is preferably employed as the inner layer due to the corresponding ease of molding. Moreover, the materials making up the inner and outer layers consist preferably of materials which exhibit excellent reciprocal adherence. Good adherence is obtained when the same type of material is employed for both the inner and outer layers.

Any water soluble drug in this invention may be used that is not soluble nor diffusible to the outer layer, and there are no particular restrictions in terms of molecular weight and so forth. However, the advantages of the present invention are particularly clear with such drugs as peptides, proteins, glycoproteins, polysaccharides, and nucleic acids. The present invention is particularly appropriate for drugs that are very active even in extremely small quantities and whose sustained long-term administration is sought. The drugs may be exemplified by, but not limited to, cytokines such as interferons and interleukins; hematopoietic factors such as colony-stimulating factors and erythropoietin; hormones such as growth hormone, growth hormone releasing factor, calcitonin, luteinizing hormone, luteinizing hormone releasing hormone, and insulin; growth factors such as somatomedin, nerve growth factor, neurotrophic factors, fibroblast growth factor, and hepatocyte proliferation factor; cell adhesion factors; immunosuppressants; enzymes such as asparaginase, superoxide dismutase, tissue plasminogen activating factor, urokinase, and prourokinase; blood coagulating factors such as blood coagulating factor VIII; proteins involved in bone metabolism such as BMP (bone morphogenetic protein); and antibodies. The interferon may be alpha, beta, gamma, or any other interferons or any combination thereof. Likewise, the interleukin may be IL-1, IL-2, IL-3, or any others, and the colony-stimulating factor may be multi-CSF (multipotential CSF), GM-CSF (granulocyte-macrophage CSF), G-CSF (granulocyte CSF), M-CSF (macrophage CSF), or any others.

Drugs that can be applied in drug formulations according to the present invention may be further exemplified by low-molecular-weight drugs such as water-soluble anticancer agents, antibiotics, anti-inflammatory drugs, alkylating agents, and immunosuppressants. Examples of these drugs include adriamycin, bleomycins, mitomycins, fluorouracil, peplomycin sulfate, daunorubicin hydrochloride, hydroxyurea, neocarzinostatin, sizofiran, estramustine phosphate sodium, carboplatin, beta-lactams, tetracyclines, aminoglycosides, and phosphomycin.

The drug formulation of the present invention may contain two or more drugs depending on the disease and method of application.

The inner layer may contain various medically acceptable swelling agents in order to control or modulate the release rate. The invention can use any swelling agent that is soluble in water and can essentially induce inner layer swelling. A single swelling agent or a mixture of two or more swelling agents can be used. Preferred examples of swelling agents include materials of biological origin such as albumin and gelatin, salts such as sodium chloride, and amino acids such as glycine. Albumin and so forth, in addition to functioning as swelling agents, can contribute to drug stabilization. When the inner layer is silicone and the drug is a peptide, protein, glyco-protein, polysaccharide or nucleic acid, albumin is preferable as swelling agent. Moreover, some of the previously mentioned water-soluble drugs, besides exhibiting therapeutic activity, are substances that themselves exhibit the swelling effect under consideration. Substances of this type are exemplified by electrolytes such as tetracycline hydrochloride. It will not be necessary to employ a swelling agent in such cases, but a swelling agent may still be used on an optional basis. When the inner layer is a material that does not swell in water and the drug used does not exhibit swelling pressure, the addition of swelling agent becomes mandatory, whereas it is optional when a water-swelling material is employed. In addition, the inner layer may contain additives such as the medically acceptable stabilizers, preservatives, analgesics, dissolution auxiliaries, and so forth.

The combined quantity of drug, swelling agent, and additive present in the inner layer is not particularly specified provided that dispersion and molding are substantially possible. This quantity will vary as a function of the inner and outer layer materials, but the combined quantity of drug, swelling agent, and additive preferably should not exceed 50 weight %. The drug content will of course vary in accordance with the type of drug, the disease under treatment and its severity, and so forth.

The drug formulation of the present invention may have a rod-like shape, for example it is selected from circular cylinders, prisms, and elliptical cylinders. When the device will be administered using an injector-type instrument, a circular cylindrical device will be preferred since the injector body and the injection needle typically have a circular cylindrical shape.

The inner layer of the drug formulation of the present invention, viewed in right section, may contain two or more layers containing different water-soluble drugs. These layers may take the form of concentric circles with a single center of gravity or may appear as a plural number of inner layers whose respective centers of gravity lie at different points in the cross section. When the drug formulation contains more than one inner layer there may be one or more drugs present in the inner layers. For example, the drugs may be present such that each layer contains a different drug or there is more than one drug in one or all of the inner layers.

Figure 2A:
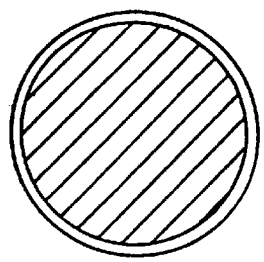
FIG. 2 contains sectional views of an embodiment of the drug formulation of the present invention.
Figure 2B:
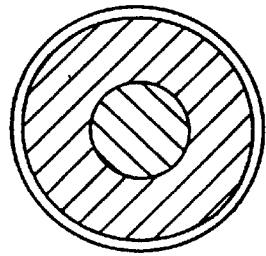
Figure 2C:
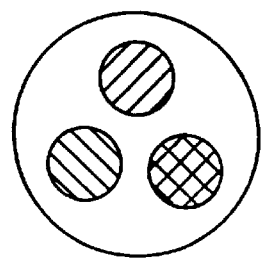

FIG. 1 contains an oblique view of the exterior of one embodiment of the drug formulation according to the present invention, and FIG. 2 depicts cross sections for this embodiment. FIG. 2 depicts, respectively, (a) the cross section of a double-layer drug formulation, (b) the cross section of a drug formulation with a single center of gravity in the device cross section, and (c) the cross section of a drug formulation having multiple centers of gravity in the device cross section.

The size of the drug formulation of the present invention may be relatively large in the case of insertion in a surgical zone or in a body cavity, and in such cases the cross-sectional diameter is preferably less than or equal to 5 mm and the axial length is preferably less than or equal to 50 mm. The cross-sectional diameter is more preferably 0.5 to 3 mm and the axial length is more preferably on the order of 5 to 35 mm. In the case of subcutaneous administration using an injector-type instrument, the configuration should be circular cylindrical, and the cross-sectional diameter in this case is preferably 0.5 to 1.7 mm and the axial length is preferably 10 to 30 mm.

The thickness of the outer layer should be selected as a function of the material properties and the desired release rate. The outer layer thickness is not critical as long as the specified functions of the outer layer are fulfilled. The outer layer thickness is preferably 0.05 mm to 3 mm, more preferably 0.10 mm to 1 mm, and even more preferably 0.15 mm to 0.2 mm.

Although drug formulations according to the present invention for the most part will have a double-layer structure, in order to achieve long-term zero-order release, the ratio of the axial length of the drug formulation to the cross-sectional diameter of the inner layer must in any case be one or more and is preferably two or more and more preferably five or more.

On the subject of fabrication of the drug formulation of the present invention, the drug-containing inner layer and the water-impermeable outer layer may be fabricated separately or simultaneously. A circular cylindrical drug formulation with a single center of gravity in the device cross section can be fabricated, for example, by the following methods: (i) initial fabrication of a rod-shaped inner layer followed by coating the rod with a liquid containing dissolved outer layer material and drying; (ii) insertion of a separately fabricated inner layer into a tube fabricated from outer layer material; or (iii) simultaneous extrusion and molding of the inner and outer layers using a nozzle. However, the fabrication method is not limited to these examples. When a water-impermeable outer layer cannot be obtained in a single operation, it will then be necessary, for example, to repeat the outer layer fabrication process until water permeation can be prevented. In any case, the resulting composition is subsequently cut into suitable lengths. Successive cutting yields a drug formulation according to the present invention having both ends open. A drug formulation with an open end at one terminal may be fabricated by dipping one terminal of the drug formulation into a solution which dissolves the outer-layer material and drying it, or by covering one terminal end of the drug formulation with a cap made from the outer-layer material. In addition the fabrication may comprise insertion of the inner layer into an outer-layer casing with a closed-end at one terminal, which are separately produced, and also formation of the inner layer in said casing.

The mechanism by which a water-soluble drug uniformly dispersed in a hydrophobic polymer carrier is released to the exterior is based on the aforementioned channeling and cracking phenomena. The heretofore known matrix-type drug formulations give an uncontrollable drug release because, upon contact with an aqueous medium, water immediately penetrates unrestrictedly into the interior of the device over the entire surface. In contrast to this, as described above only an end(s) of the inner layer comes into contact with the external environment in the case of the drug formulation according to the present invention, and as a result only a limited region rather than the entire surface is initially subject to channeling. In addition, the outer layer, due to its characteristic functional design, is able to exercise suitable control of inner layer cracking. Through these means, the present invention is able to exercise suitable control of water infiltration into the interior and is thereby able to achieve long-term zero-order release.

Drug release from the drug formulation of the present invention can be adjusted or modulated by a number of techniques. For example, modifying the type of outer layer material and/or adjusting the outer layer thickness functions to alter the pressure applied to the inner layer. This influences the frequency of cracking and thus results in a modification of the drug release rate.

Precise control over a broad range is possible because the drug release rate and/or inner layer swelling rate can be varied by varying the drug content of the inner layer and the size and shape of the drug particles and through additive selection.

Water infiltration and drug release in the present invention occur throughout the process over a constant surface area of the inner layer in contact with the external environment. As a result, the period of sustained release can be controlled by selecting the axial length without change in the release rate.

As described hereinbefore, the drug formulation according to the present invention provides long-term zero-order release, and as a result the blood concentration of a drug can be maintained for extended periods of time. This effect cannot be expected from the heretofore known drug formulations. Thus, pharmacological effects unknown to date become conceivable even for already known drugs.

The drug formulations of the present invention can be used in both human and animal applications.

So that those skilled in the art can understand and appreciate the invention taught herein, the following examples are presented, it being understood that these examples should not be used to limit the scope of this invention found in the claims attached hereto.

EXAMPLE 1

1.5 g lyophilized human serum albumin (HSA) powder was mixed into 3.5 g of part A of Silastic® Medical Grade ETR Elastomer Q7-4750, and 1.5 g HSA powder was mixed into 3.5 g of part B of Silastic® Medical Grade ETR Elastomer Q7-4750. The two mixtures were then combined, followed by extrusion through an aperture with a diameter of 1.9 mm by the application of pressure, and curing at room temperature. The aforementioned parts A and B differ somewhat in composition, and only after the two parts were combined a crosslinking reaction began and curing took place. Cutting gave a drug formulation (1) having an inner layer diameter of 2 mm and a length of 10 mm.

The cured extrudate, produced by the same process as above, was also coated with a 0.2-mm thick outer layer by immersion in a 10% toluene dispersion of Silastic® Medical Grade ETR Elastomer Q7-4750 (1:1 mixture of parts A and B) and drying. This was then cut to obtain a drug formulation (2) having an inner layer diameter of 2 mm and a length of 10 mm.

TEST EXAMPLE 1

Figure 3:
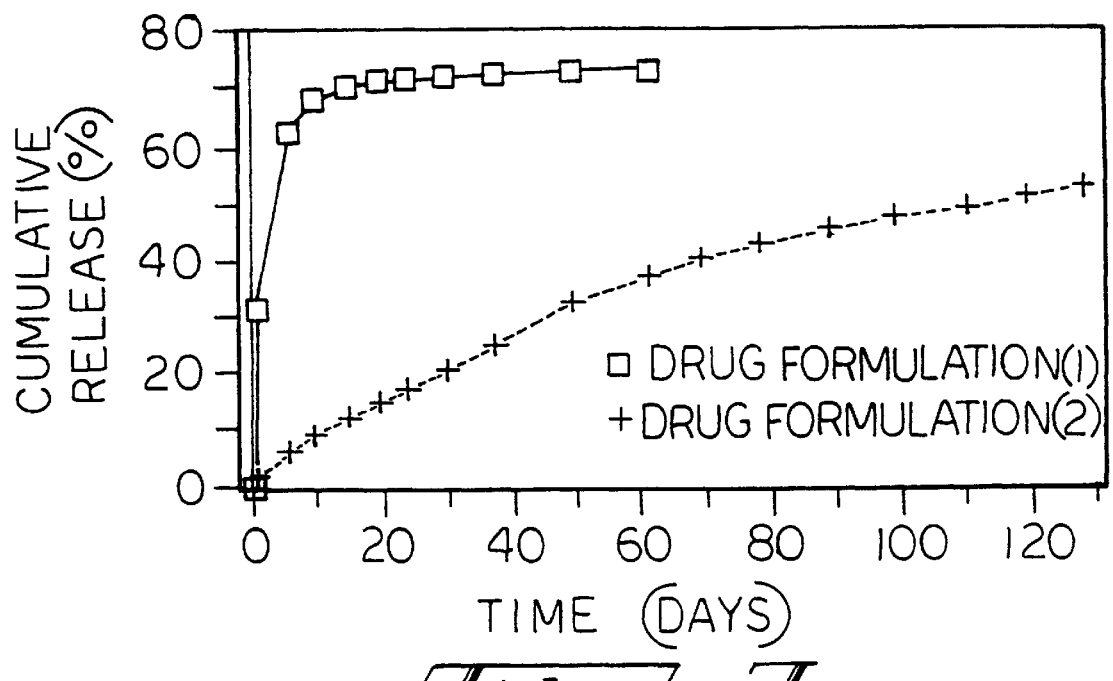
FIG. 3 contains a graph which shows the difference in HSA release behavior between a matrix-type drug formulation (drug formulation (1)) and a drug formulation of the present invention (drug formulation (2)).

Drug formulations (1) and (2) fabricated in Example 1 were respectively placed in 3 mL phosphate buffer at 37° C. and left undisturbed. The amount of HSA released from each drug formulation was measured by spectrophotometry in order to determine the cumulative percent release. These results are reported in FIG. 3. Compared with the matrix-type drug formulation (1), which exhibited a very rapid initial release, the drug formulation according to the present invention (2) provided sustained zero-order release over a period of months by virtue of its ability to control water infiltration. That is, when an outer layer is provided in conformity with the present invention, a very rapid initial release is prevented and a sustained zero-order release over a period of months can be achieved.

EXAMPLE 2

Lyophilized HSA powder (0.64 g) was dispersed in 9 mL of a 10% ethylene-vinyl acetate copolymer (EVA)/methylene chloride solution, which was solidified by cooling. This was dried at −20° C. and then at room temperature. After cutting into narrow strips (5 mm×0.8 mm×20 mm), immersion in 10% EVA/methylene chloride solution, and drying at room temperature, both ends were cut off to yield a drug formulation (3) having an inner layer size of 5 mm×0.8 mm×10 mm and an outer layer thickness of 0.05 mm.

TEST EXAMPLE 2

Figure 4:
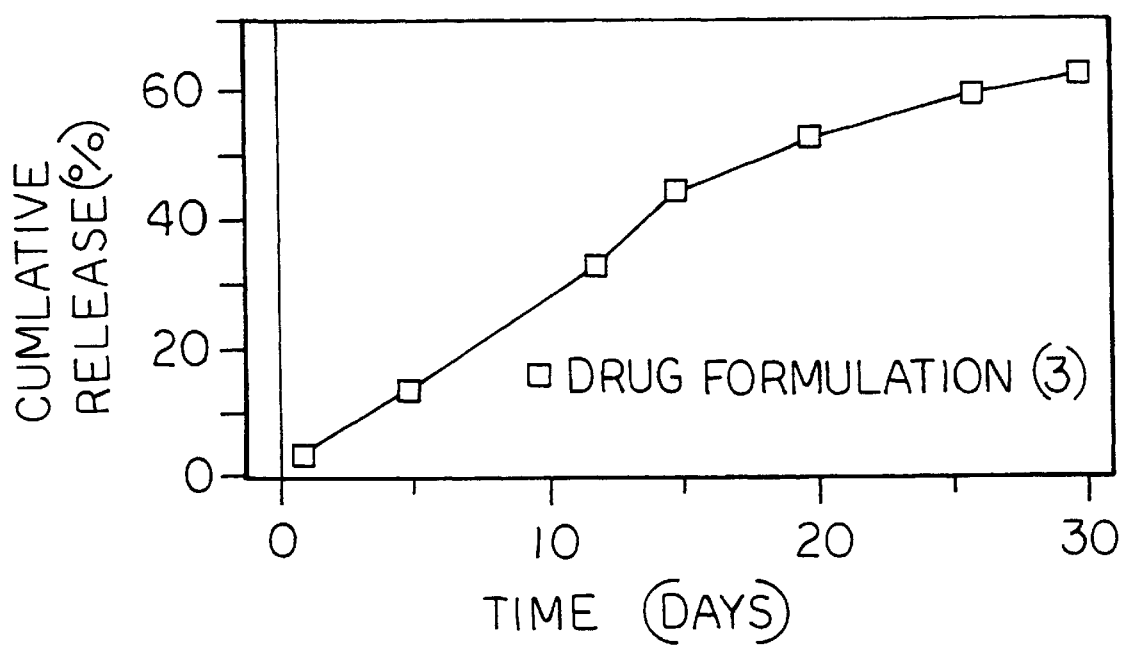
FIG. 4 contains a graph which shows the HSA release behavior from a drug formulation that uses ethylene-vinyl acetate copolymer as the inner layer material.

Drug formulation (3) fabricated in Example 2 was placed in 3 mL of phosphate buffer at 37° C. and then left undisturbed. The amount of HSA released from the drug formulation was measured by spectrophotometry in order to determine the cumulative percent release. These results are reported in FIG. 4. The use of EVA as carrier again gave a zero-order release just as for drug formulation (2) of Example 1.

EXAMPLE 3

Tetracycline hydrochloride (0.15 g) was mixed with 0.35 g of poly(lactic acid-glycolic)acid copolymer (PLGA, the weight ratio of lactic acid/glycolic acid=75/25 in the polymer) in the presence of methylene chloride and the mixture was extruded from a syringe. After drying at room temperature, the material was immersed in 10% EVA/methylene chloride solution and then re-dried at room temperature. Cutting both ends gave drug formulation (4) having an inner layer diameter of 1.3 mm and a length of 10 mm and an outer layer thickness of 0.05 mm.

TEST EXAMPLE 3

Figure 5:
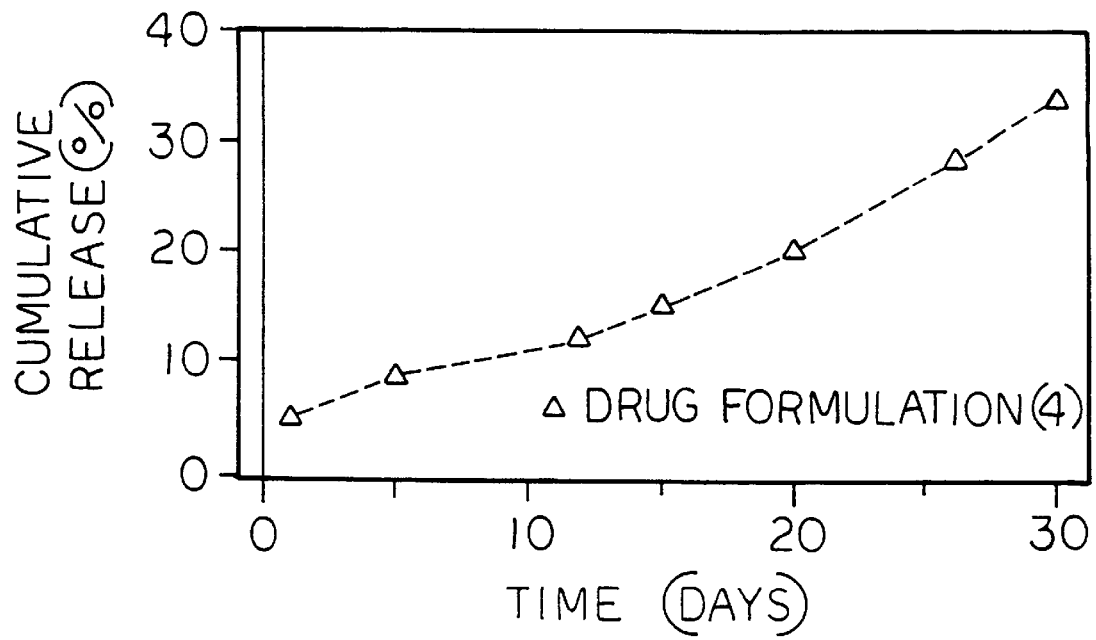
FIG. 5 contains a graph which shows the tetracycline hydrochloride release behavior from a drug formulation that uses poly(lactic acid-glycolic acid)copolymer as the inner layer material.

Drug formulation (4) fabricated in Example 3 was placed in 3 mL of phosphate buffer at 37° C. and then left undisturbed. The amount of tetracycline hydrochloride released from the device was measured by spectrophotometry in order to determine the cumulative percent release. These results are reported in FIG. 5. In this case, the controlled release of a low-molecular-weight drug, tetracycline hydrochloride, was achieved using biodegradable PLGA as the inner layer material.

EXAMPLE 4

Tetracycline hydrochloride (0.38 g) was dispersed in 9 mL of 10% EVA/methylene chloride solution and cooled to solidification. The material was dried at −20° C. and then at room temperature. After cutting into narrow strips (5 mm×1 mm×20 mm), immersion in 10% EVA/methylene chloride solution, and then drying at room temperature, both ends were cut off to yield drug formulation (5) having an inner layer size of 5 mm×1 mm×10 mm and an outer layer thickness of 0.05 mm.

EXAMPLE 5

Tetracycline hydrochloride (0.38 g) was dispersed in 9 mL of 10% EVA/methylene chloride solution and cooled to solidification. This was dried at −20° C. and then at room temperature. After cutting into narrow strips (5 mm×0.9 mm×20 mm), immersion in a 10% methylene chloride solution of poly(lactic acid-glycolic)acid copolymer (PLGA, lactic acid/glycolic acid ratio in polymer=75/25), and then drying at room temperature, both ends were cut off to yield drug formulation (6) having an inner layer size of 5 mm×0.9 mm×10 mm and an outer layer thickness of 0.14 mm.

EXAMPLE 6

A mixture of 42 mL of 14 MU/mL interferon solution (desalted/concentrated Sumiferon®) and 24.33 mL 25% HSA solution (Buminate®) was lyophilized to yield an IFN/HSA powder. 0.75 g of this IFN/HSA powder was mixed with 1.75 g of part A of Silastic® Medical Grade ETR Elastomer Q7-4750, and 0.75 g of the IFN/HSA powder was mixed with 1.75 g of part B of Silastic® Medical Grade ETR Elastomer Q7-4750. The two mixtures were combined, introduced into a container with a 1.9 mm aperture, extruded by the application of pressure, and then left to cure at room temperature. Coating with a 0.2-mm thick outer layer was carried out by immersion in a 10% toluene dispersion of Silastic® Medical Grade ETR Elastomer Q7-4750 (1:1 mixture of part A and part B) and drying. Cutting then yielded a drug formulation (7) having an inner layer diameter of 2 mm and a length of 10 mm.

EXAMPLE 7

The drug formulations indicated in the following Table 1 were fabricated according to the method of Pharmaceutical Technology, June 1985, pages 39–49. Utilizing this method, Dow Corning® MDX-4-4210 Medical Grade Elastomer was mixed with vulcanizing agent at the ratio of 10:1, and then thereto lyophilized human serum albumin (HSA) powder was admixed in the specified proportions. After defoaming, the mixture was filled into a TOP® silicone tube and cured. This was then cut to yield the particular device.

TABLE 1

|  | HSA particle size, content | inner layer diameter | outer layer material, thickness | device length |
|---|---|---|---|---|
| device (8-1) | 250–425 μm, 30% | 8.0 mm | silicone, 1.5 mm | 5 mm |
| device (8-2) | 250–425 μm, 30% | 8.0 mm | silicone, 1.5 mm | 8 mm |
| device (8-3) | 250–425 μm, 30% | 8.0 mm | silicone, 1.5 mm | 16 mm |

TEST EXAMPLE 4

Each device fabricated in Example 7 was placed in 3 mL of phosphate buffer at 37° C. and then left undisturbed, and the weight of the device was measured at each sampling. The quantity of water (g) contained in the device was calculated from the following formula.

water infiltration (g)=wet weight of device−[initial device weight−cumulative HSA release (g)]    Formula 1;

Saturation was considered to have been reached when water infiltration no longer exceeded that at the previous measuring, and the number of days at the previous measuring was taken as the time required to reach saturation. The results are reported in Table 2.

TABLE 2

|  | inner layer diameter:length | time required for water infiltration to reach saturation |
|---|---|---|
| device (8-1) | 2:1 | approx. 2 weeks |
| device (8-2) | 1:1 | ≧4 weeks |
| device (8-3) | 1:2 | ≧4 weeks |

Figure 6:
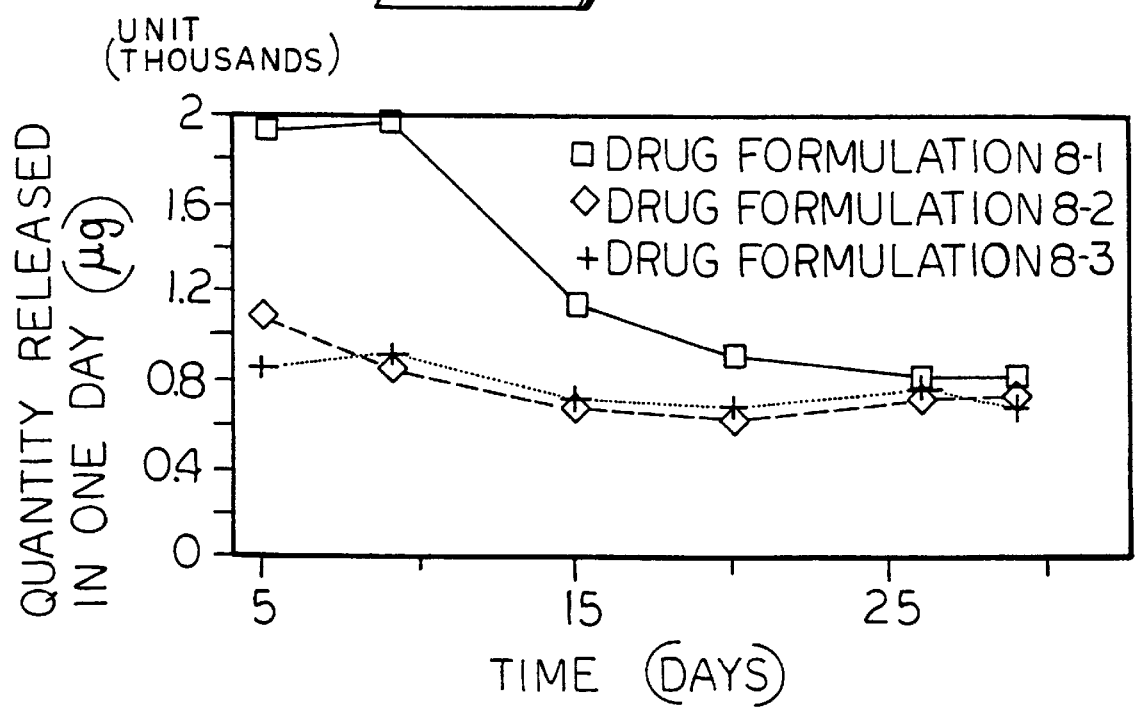
FIG. 6 contains a graph which shows the quantities of HSA release (per day) from drug formulations with differing lengths (drug formulations (8-1), (8-2), and (8-3)).

In addition, the amount of HSA released from the drug formulation was measured by spectrophotometry. The quantity of HSA release (per day) from each device is reported in FIG. 6.

The results reported in Table 2 show that when the ratio of the axial length of the inner layer to its cross-sectional diameter was one or more, the time for water infiltration to reach saturation was extended by a factor of two. These results thus confirmed that, by extending the length of the drug formulation as in the present invention, the release behavior is changed to a nearly constant zero-order rate during the experimental period from burst behavior (ie. initially large drug release followed by a tapering-off period).

What is claimed is:

1. A controlled release drug formulation in the form of a cylindrical rod having an axial length comprising:
    (a) a nondisintegrating inner layer having a cross-sectional diameter and a circumference wherein said inner layer is comprised of a biocompatible hydrophobic material selected from the group consisting of polyesters, polyamino acids, silicones, ethylene-vinyl acetate copolymers and polyvinyl alcohols that contains at least one uniformly dispersed water-soluble drug as the only active agent(s), and
    (b) an outer layer comprised of a biocompatible hydrophobic polymer wherein said outer layer surrounds the circumference of the inner layer and the outer layer is impermeable to water and is capable of controlling the swelling of the inner layer;
    wherein the ratio of the axial length of the drug formulation to the cross-sectional diameter of the inner layer is one or more and at least one end of the inner layer is open so as to come into contact with any external environment, and wherein the drug is released at a controlled rate over a prolonged period of time exclusively through said open end.

2. A drug formulation as claimed in claim 1 which is of a type for intracorporeal implantation.

3. A drug formulation as claimed in claim 1 wherein the inner layer is comprised of a biocompatible material selected from the group consisting of polyesters, polyamino acids, silicones, ethylene-vinyl acetate copolymers, and polyvinyl alcohols.

4. A drug formulation as claimed in claim 3 wherein the inner layer is comprised of a silicone.

5. A drug formulation as claimed in claim 1 wherein the outer layer is comprised of a biocompatible material selected from the group consisting of polyesters, hydrophobic polyamino acids, polyanhydrides, silicones, polytetrafluoroethylenes, polyethylenes, polypropylenes, polyurethanes, polyacrylates, polymethacrylates, and ethylene-vinyl acetate copolymers.

6. A drug formulation as claimed in claim 1 wherein the inner layer is comprised of a biocompatible material selected from the group consisting of polyesters, polyamino acids, silicones, ethylene-vinyl acetate copolymers, and polyvinyl alcohols, and the outer layer is comprised of a biocompatible material selected from the group consisting of polyesters, hydrophobic polyamino acids, polyanhydrides, silicones, polytetrafluoroethylenes, polyethylenes, polypropylenes, polyurethanes, polyacrylates, polymethacrylates, and ethylene-vinyl acetate copolymers.

7. A drug formulation as claimed in claim 5, wherein the outer layer is comprised of a silicone.

8. A drug formulation as claimed in claim 1 wherein both the inner and outer layers are comprised of silicone.

9. A drug formulation as claimed in claim 1 wherein the ratio of the axial length of the drug formulation to the cross-sectional diameter of the inner layer is two or more.

10. A drug formulation as claimed in claim 1 wherein the ratio of the axial length of the drug formulation to the cross-sectional diameter of the inner layer is five or more.

11. A drug formulation as claimed in claim 1 wherein the drug is selected from the group consisting of peptides, proteins, glyco-proteins, polysaccharides and nucleic acids.

12. A drug formulation as claimed in claim 1 wherein the drug is selected from the group consisting of cytokines, hematopoietic factors, hormones, growth factors, cell adhesion factors, immunosuppressants, enzymes, blood coagulating factors, proteins involved in bone metabolism, antibodies, anticancer agents, antibiotics, anti-inflammatory drugs, and alkylating agents.

13. A drug formulation as claimed in claim 11, wherein the drug is selected from the group consisting of cytokines, hematopoietic factors, hormones, growth factors, adhesion factors, immunosuppresants, enzymes, blood coagulating factors, proteins involved in bone metabolism, and antibodies.

14. A drug formulation as claimed in claim 1 wherein a swelling agent is additionally present in the inner layer.

15. A drug formulation as claimed in claim 14 wherein the swelling agent is selected from the group consisting of albumin, gelatin, salts, and amino acids.

16. A drug formulation as claimed in claim 15 wherein the drug is selected from the group consisting of cytokines, hematopoietic factors, hormones, growth factors, cell adhesion factors, immunosuppressants, enzymes, blood coagulating factors, proteins involved in bone metabolism, and antibodies.

17. A drug formulation as claimed in claim 1 wherein the drug formulation has a cross-sectional diameter of less than or equal to 5 mm and an axial length of less than or equal to 50 mm.

18. A drug formulation as claimed in claim 1 wherein the drug formulation has a cross-sectional diameter of 0.5 mm to 3 mm and an axial length of 5 to 35 mm.

19. A drug formulation as claimed in claim 1 wherein the outer layer has a thickness of 0.05 mm to 3 mm.

20. A drug formulation as claimed in claim 17 wherein the outer layer has a thickness of 0.10 mm to 1 mm.

21. A drug formulation as claimed in claim 17 wherein the outer layer has a thickness of 0.15 mm to 0.2 mm.

22. A drug formulation as claimed in claim 1 wherein both ends of the inner layer are open so as to come into contact with the external environment.

23. A method for controlling the rate of release of a drug from a drug formulation in the form of a cylindrical rod by controlling water infiltration into the drug formulation wherein said drug formulation has an axial length and comprises (a) a nondisintegrating inner layer having a cross-sectional diameter and a circumference wherein said inner layer is comprised of a biocompatible hydrophobic material selected from the group consisting of polyesters, polyamino acids, silicones, ethylene-vinyl-acetate copolymers and polyvinyl alcohols that contains at least one uniformly dispersed water-soluble drug as the only active agent(s), and (b) an outer layer comprised of a biocompatible hydrophobic polymer wherein said outer layer surrounds the circumference of the inner layer and the outer layer is impermeable to water and is capable of controlling the swelling of the inner layer;

wherein the ratio of the axial length of the drug formulation to the cross-sectional diameter of the inner layer is one or more and at least one end of the inner layer is open so as to come into contact with any external environment, and wherein the drug is released at a controlled rate over a prolonged period of time exclusively through said open end.

* * * * *